United States Patent [19]

Wohler, Jr.

[11] Patent Number: 4,564,024

[45] Date of Patent: Jan. 14, 1986

[54] ELECTRO-EJACULATOR PROBE

[76] Inventor: Wilson H. Wohler, Jr., 1202 N. Bell St., San Angelo, Tex. 76905

[21] Appl. No.: 628,201

[22] Filed: Jul. 2, 1984

[51] Int. Cl.$^4$ .............................................. A61N 1/18
[52] U.S. Cl. .................................. 128/788; 128/419 S
[58] Field of Search ............... 128/788, 794, 800, 784, 128/421, 419 S, 642

[56] References Cited

U.S. PATENT DOCUMENTS 2,808,834 10/1957 Marden ............................ 128/419 S
4,124,028 11/1978 Gallo ................................ 128/419 S

OTHER PUBLICATIONS

Marden; "New Advances in the Electroejaculation of the Bull"; *J. Dairy Science* 19, 11-1953, pp. 556-561.
Toso et al.; "Electro-Eyaculador"; *Sezione III;* 1964, pp. 715-718.
Healey et al.; "Construction of Rectal Electrodes for Electro-Ejaculation"; *J. Reprod. Fert.* (1966) 11, pp. 299-301.
Dziuk et al.; "Technique of Electroejaculation and its Use in Dairy Bulls"; *Univ. of Minn. Scientific Journal Series Paper* #3108, 1954; pp. 1035-1041.

*Primary Examiner*—Lee S. Cohen
*Assistant Examiner*—Angela D. Sykes
*Attorney, Agent, or Firm*—Wendell Coffee

[57] ABSTRACT

An electro-ejaculator probe is inserted into the rectum of a restrained bovine bull. Electrical current is passed from electrodes located on the probe primarily to the nerves controlling erection and ejaculation. As little as possible, current is passed to the nerves registering pain. Electrical stimulation of these nerves results in ejaculation. Voids or pockets in the probe receive any fecal matter which might otherwise insulate the electrodes from the intestine wall. The ejaculated semen is collected for analysis or artificial insemination.

3 Claims, 3 Drawing Figures

ELECTRO-EJACULATOR PROBE

BACKGROUND OF THE INVENTION (1) Field of the Invention

This invention relates to the electrical induction of ejaculation of semen from male mammals. More particularly, this invention relates to ejaculation of semen from bovine bulls.

(2) Description of the Prior Art

Three methods are used to induce ejaculation from bovine bulls. They are rectal massage, use of an artificial vagina, and electro-ejaculation.

Rectal massage involves introducing the operators lubricated glove hand into the rectum to remove feces and identify pelvic structures. After this is accomplished, each seminal vesicle is massaged in a cranial to caudal direction to stimulate secretion of seminal fluid. Next, the ampullae of the vasa differentia are alternately massaged in a cranial to caudal direction. An assistant collects the emission from the urethral orifice when the emission changes from a clear to a milky color.

Another method in use to induce ejaculation from bovine bulls is the artificial vagina method. This method produces the highest quality ejaculate because it is considered characteristic of the bull's physiologic ejaculate. Disadvantages of this method include the expenditure of a great deal of time, particularly when an inexperienced bull is involved, the need for another animal to serve as a mount and danger of injury to the operator while handling the animals.

A third method of inducing ejaculation is the insertion of an electro-ejaculator probe into the rectum to stimulate the nerves involved in erection and ejaculation. Electro-ejaculator probes before my invention were constructed of wood, plastic or rubber and fabric composition with electrodes mounted on the probe either lengthwise or circumferentially. Recent advances in the art have shown that the method is more effective and less painful for the animal if the electrodes are mounted on the probe's ventral surface. This facilitates greater stimulation of the nerves more directly involved with erection and ejaculation, and less stimulation of sensory nerves of the spinal area which transmit pain inpulses.

The probe is cylindrical in shape with a continuous or solid wall. The solid wall construction of the probe and the peristallic action or abdominal pressure propels fecal material rearward which may force the probe out of the rectum or cause the separation of the electrodes from the inner face of the bowel, thus reducing current transmissions.

A discussion of semen collection and electro-ejaculator probes is found in Amstutz, H. E., D.V.M., ed., *Bovine Medicine and Surgery*, Second Edition, Volume 2, 1980, American Veterinary Publications, Inc., Santa Barbara, Calif., pp. 996 et seq. and 1012 et seq.

SUMMARY OF THE INVENTION (1) New Functions and Surprising Results

I have invented an electro-ejaculator probe for use in electrical induction of ejaculation utilizing the electrodes of the probe as the primary structure of the device. Electrical wires run through the handle and connect to the electrodes. Electrical current transmitted from a power source to the electrodes stimulates nerves involved in erection and ejaculation.

A result of my design is a probe which is not circumferentially solid or continuous. This allows feces being propelled rearward to move into the void or cavity or pocket of the probe body rather than cause separation of the electrodes from the bowel wall. Less separation (better contact with the inner face of the bowel wall) results in greater control and regularity of the electrical current transmissions. This results in an increased collection success rate and a decreased collection time.

Therefore it may be seen that the function of the combination of the parts of my invention far exceeds the total of the functions of the individual elements such as electrodes, wires, electricity, etc.

(2) Objects of this Invention

An object of this invention is to electrically induce erection and ejaculation in mammals.

Other objects of my invention are to prevent expulsion of the probe from the rectum, maintain a steady current flow from the probe to the bowel wall and achieve a high collection success rate with a short collection time.

Another object of my invention is to achieve the above in a manner which minimizes the pain and discomfort experienced.

Further objects are to achieve the above with a device that is sturdy, compact, durable, lightweight, simple, safe, efficient, ecologically compatible, energy conserving, and reliable, yet inexpensive and easy to manufacture, operate and maintain.

Other objects are to achieve the above with a method that is ecologically compatible, energy conserving, rapid, efficient, and inexpensive, and does not require highly skilled people to operate, and maintain.

The specific nature of the invention, as well as other objects, uses, and advantages thereof, will clearly appear from the following description and from the accompanying drawing, the different views of which are not scale drawings.

DESCRIPTION OF THE PREFERRED EMBODIMENT

Figure 1:
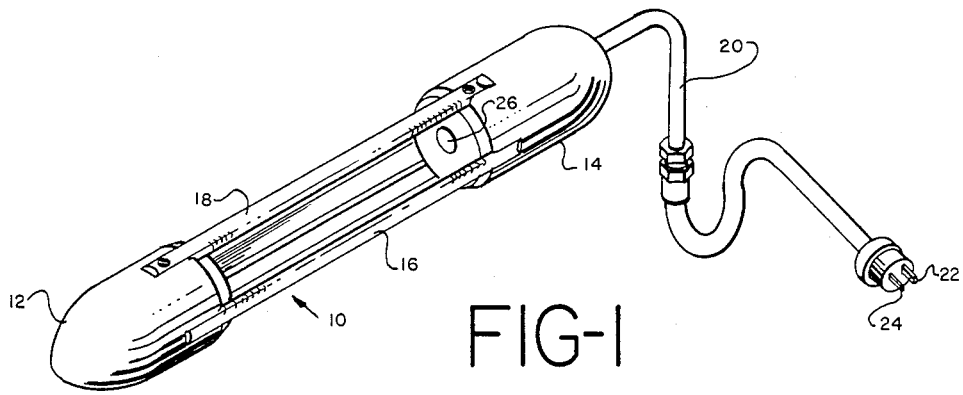
FIG. 1 is a perspective view of one embodiment of my invention.

Electro-ejaculator probe 10 has a front and back with bullet-shaped nose 12 at the front and rounded end 14 at the back with the outer surfaces of nose 12 and end 14 lying along a cylindrical boundary, profile, outline, silhouette, envelope or delineation which is about an elongated axis. In this embodiment nose 12 and end 14 are constructed of wood, but other materials of construction compatible with bovine intestines would work equally well. Additionally, if this material will conduct electrical current, it should be insulated from the elongated electrodes. Dorsal electrode or bar 18 and elongated electrodes 16 and 17 extend from nose 12 to end 14 along the cylindrical profile, and parallel to the elongated axis. Elongated electrodes 16, 17 and 18 are structurally attached to nose 12 and end 14. In this particular embodiment they are the sole structural support between nose 12 and end 14. They are attached by bolts 19 extending into axial bore 21 which is later filled, as for example with Plaster of Paris 26. The gaps between the electrodes and nose 12 and end 14 are also filled as shown at 28. Other embodiments include any additional structural supports that leaves at least one pocket or cavity or void in the cylindrical profile with passages for feces to move within the cylindrical profile. Elongated electrodes 16 and 17 are constructed of electrically conductive materials which are compatible with bovine intestines.

Handle 20 extends axially from end 14. Electrical wires 22 and 24 extend through handle 20 which is conveniently formed of conduit tubing. The wires 22 and 24 connect to elongated electrodes 16 and 17. In this particular embodiment, handle 20 is a tail extending from end 14 and curving down. But it should be understood that my invention will work equally well with different handles.

Figure 2:
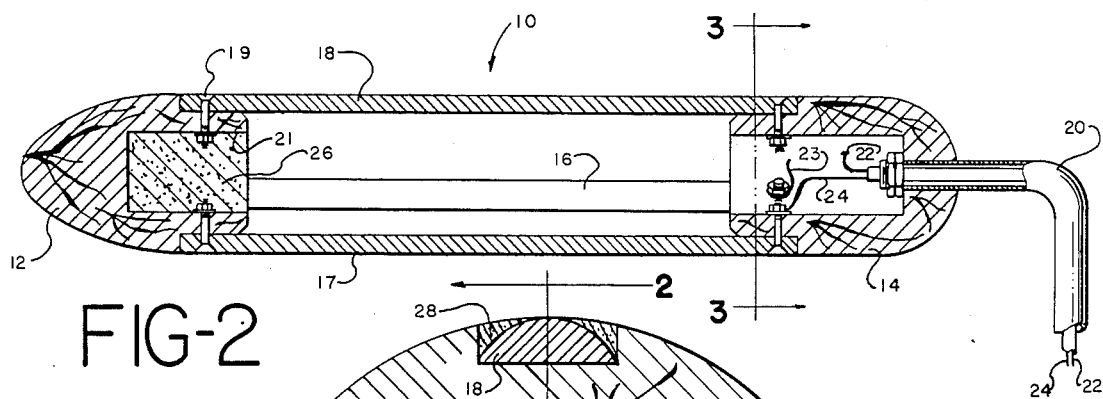
FIG. 2 is an axial, sectional view thereof taken on line 2—2 of FIG. 3.
Figure 3:
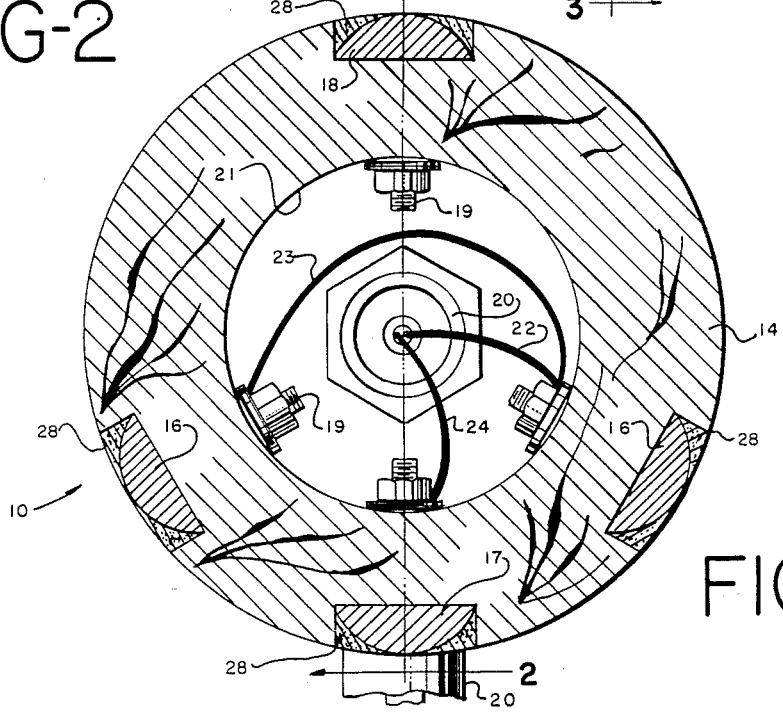
FIG. 3 is a cross sectional view thereof taken on line 3—3 of FIG. 2.

The wire 22 connects to one lateral electrode 16. Jumper 23 extends from one lateral electrode 16 to the other. Wire 24 is connected to the ventral electrode 17. There is a voltage or electrical potential between the wires. The two lateral electrodes 16 are electrically connected together. The electrical potential is between the lateral and ventral electrodes. The dorsal bar or electrode 18 has no electrical potential connected to it. The electrical wiring from the conduit or handle 20 is within the axial bore 21 within the end 14. After all the wiring is in place, the bore 21 is conveniently filled with a filling such as Plaster of Paris 26. This has not been shown in FIGS. 2 and 3 so that the wires may be shown. However, the Plaster of Paris is shown in FIGS. 1 and in the nose 12 of FIG. 2.

As it may be seen, in the drawings the handle extends straight down. The dorsal bar or electrode 18 is at the top. The ventral electrode 17 is diametrically opposite the top electrode 18. The lateral electrodes 16 are spaced about 45° on either side of the ventral electrode 17.

The electrodes 16, 17, and 18 help in part to define the cylindrical profile. They also define the fecal pocket within them between the front nose 12 and the end 14. The spaces between the electrodes would be an opening or passages into the pocket.

In operation, electro-ejaculator probe 10 is lubricated and inserted into the rectum of a restrained bovine bull. Handle 20 is used to position the probe with dorsal bar 18 placed uppermost. Electrical current is passed between elongated electrodes 16 and 17 to nerves involved in erection and ejaculation. With proper control of the electrical current, an ejaculate and erection equal in quality and quantity to that produced with other methods may be obtained.

The embodiment shown and described above is only exemplary. I do not claim to have invented all the parts, elements or steps described. Various modifications can be made in the construction, material, arrangement, and operation, and still be within the scope of my invention.

The limits of the invention and the bounds of the patent protection are measured by and defined in the following claims. The restrictive description and drawing of the specific example above do not point out what an infringement of this patent would be, but are to enable the reader to make and use the invention.

I claim as my invention:

1. In an electro-ejaculator probe having
   a. a cylindrical profile about an elongated axis,
   b. a front and back,
   c. a bullet-shaped nose at the front,
   d. a rounded structure at the back,
   e. the front and back having outer surfaces along the cylindrical profile,
   f. a plurality of elongated electrodes
      (i) along the cylindrical profile,
      (ii) parallel to the axis, and
      (iii) structurally attached to the front and back,
   g. a handle attached to the back, and
   h. electrical wires connected to the electrodes extending through the handle;
   j. wherein the improved structure comprises:
   k. a fecal pocket within the cylindrical profile between the front and back,
   l. said pocket opening to outside the profile between adjacent electrodes.

2. The invention as defined in claim 1 wherein:
   m. said electrical wires are adapted to have an electrical potential between them,
   n. at least four of said electrodes being:
      (i) a dorsal electrode,
      (ii) a ventral electrode, and
      (iii) two lateral electrodes,
   o. and the wires connected so that:
      (i) the lateral electrodes are connected together,
      (ii) the electrical potential is between the lateral and ventral electrodes, and
      (iii) the dorsal electrode has no electrical potential connected to it.

3. The process of collecting semen involving an electro ejaculator probe having
   a. a front and back
   b. a bullet-shaped nose at the front,
   c. a rounded structure at the back,
   d. a plurality of elongated electrodes extending from the front to back,
   e. a handle attached to the back, and
   f. electrical wires connected to the electrodes extending through the handle,
   g. wherein the improved method comprises:
   h. inserting the probe into the rectum of a restrained male,
   i. collecting fecal matter in a pocket between the front and back, thereby
   j. electrically contacting the electrodes with the inner face of the bowel, and
   k. applying electrical potential to the inner face by the electrodes.

* * * * *